United States Patent [19]

Glombik et al.

[11] Patent Number: 4,943,576
[45] Date of Patent: Jul. 24, 1990

[54] SUBSTITUTED QUINOXALYL-IMIDAZOLIDINE-2,4-DIONES, PROCESSES FOR THEIR PREPARATION, THEIR USE AS MEDICAMENTS AND PHARMACEUTICAL PREPARATIONS

[75] Inventors: Heiner Glombik, Hofheim am Taunus; Roland Utz, Messel; Hans-Jochen Lang, Hofheim am Taunus; Karl Geisen, Frankfurt am Main; Friedrich E. Beyhl, Kelkheim, all of Fed. Rep. of Germany

[73] Assignee: Hoechst Aktiengesellschaft, Frankfurt am Main, Fed. Rep. of Germany

[21] Appl. No.: 184,965

[22] Filed: Apr. 22, 1988

[30] Foreign Application Priority Data

Apr. 25, 1987 [DE] Fed. Rep. of Germany ....... 3713872

[51] Int. Cl.$^5$ ................ A61K 31/495; C07D 401/02; C07D 401/04; C07D 401/14
[52] U.S. Cl. .................................. 514/249; 514/250; 544/231; 544/344; 544/347; 544/353; 544/354; 544/356
[58] Field of Search .................. 544/353, 354, 356; 514/249

[56] References Cited

U.S. PATENT DOCUMENTS 4,734,407 3/1988 Schmidt et al. ............... 540/222

FOREIGN PATENT DOCUMENTS 3509618 9/1986 Fed. Rep. of Germany .

OTHER PUBLICATIONS

P. F. Kador et al., J. Med. Chem., vol. 28, pp. 841–849 (1985).

*Primary Examiner*—Anton H. Sutto
*Assistant Examiner*—E. Bernhardt
*Attorney, Agent, or Firm*—Finnegan, Henderson, Farabow, Garrett, and Dunner

[57] ABSTRACT

Substituted quinoxalyl-imidazolidine-2,4-diones, processes for their preparation, their use as medicaments and pharmaceutical preparations 5-Quinoxalyl-imidazolidine-2,4-diones of the formula I

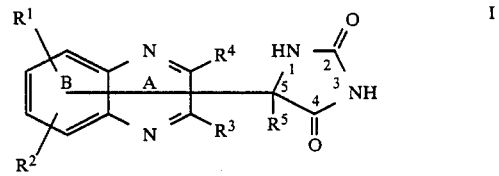

in which $R^1$, $R^2$, $R^3$, $R^4$ and $R^5$ have the meanings given, and physiologically tolerated salts thereof and processes for their preparation are described. The compounds inhibit aldose reductase and can be used as medicaments.

5 Claims, No Drawings

SUBSTITUTED QUINOXALYL-IMIDAZOLIDINE-2,4-DIONES, PROCESSES FOR THEIR PREPARATION, THEIR USE AS MEDICAMENTS AND PHARMACEUTICAL PREPARATIONS

Substances which normalize the blood glucose and insulin levels have hitherto essentially been used in the therapy of diabetes mellitus.

Compounds for influencing chronic diabetic damage and late complications have recently been described. These forms of damage and late complications include diabetic neuropathy, microangiopathy—primarily as retinopathy and as nephropathy—and cataract formation. According to recent research results, inhibitors of the enzyme aldose reductase can be used for the treatment of these diseases. The aldose reductase inhibitors with the most potent action which are known to date include spirolinked imidazolidinediones (P. F. Kador, J. H. Konoshita and N. E. Sharpless, J. Med. Chem. 28 [1985], 841).

Surprisingly, it has now been found that suitably substituted quinoxalyl-imidazolidinediones have a higher action potency in the inhibition of aldose reductase and can therefore be used for the treatment of chronic diabetic complications.

The invention therefore relates to 5-quinoxalyl-imidazolidine-2,4-diones of the formula I

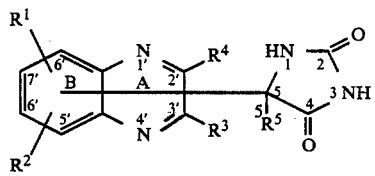

in which
the quinoxaline ring system is bonded to the imidazolidinedione via positions 2', 3', 5', 6', 7' or 8', $R^1$ and $R^2$ are identical or different and denote hydrogen, $(C_1-C_6)$-alkyl, $(C_5-C_7)$-cycloalkyl, phenyl-$(C_1-C_4)$-alkyl, naphthyl-$(C_1-C_4)$-alkyl, $(C_6-C_{12})$-aryl, a 5- or 6-membered heteroaryl ring which has sulfur, oxygen or 1 or 2 nitrogen atoms as hetero atom(s) and is optionally benzo-fused, $(C_1-C_4)$-alkoxy, halogen, halogeno-$(C_1-C_4)$-alkyl, nitro, amino or hydroxyl;

$R^3$ and $R^4$ are identical or different and denote hydrogen, $(C_1-C_6)$-alkyl, $(C_5-C_7)$-cycloalkyl, phenyl-$(C_1-C_4)$-alkyl, naphthyl-$(C_1-C_4)$-alkyl, $(C_6-C_{12})$-aryl, a 5- to 6-membered heteroaryl ring which has sulfur, oxygen or 1 or 2 nitrogen atoms as hetero atom(s) and is optionally benzo-fused, amino, nitro or hydroxyl;

$R^5$ denotes a hydrogen atom, $(C_1-C_6)$-alkyl, $(C_5-C_7)$-cycloalkyl, phenyl-$(C_1-C_4)$-alkyl, naphthyl-$(C_1-C_4)$-alkyl or $(C_6-C_{12})$-aryl, $R^3$ and $R^5$ or $R^4$ and $R^5$, if ring A is substituted by imidazolidinedione, can also together form a —$(CH_2)_n$- group, where n=2, 3 or 4, which is optionally substituted by $(C_1-C_4)$-alkyl, or, if ring B is substituted by imidazolidinedione, $R^3$ and $R^4$ can also together form a —$(CH_2)_m$— group, where m=3, 4 or 5, which is optionally substituted by $(C_1-C_4)$-alkyl,
and physiologically tolerated salts thereof.

If the imidazolidinedione radical is bonded to ring A, it replaces one of the radicals $R^3$ or $R^4$.

Preferred compounds of the formula I are those in which (a) the quinoxaline ring system is bonded to the imidazolidinedione via position 2' or 3' and $R^1$ and $R^2$ are in positions 6' and 7' respectively and denote hydrogen, $(C_1-C_4)$-alkyl, phenyl, $(C_1-C_4)$-alkoxy, halogen, halogeno-$(C_1-C_4)$-alkyl, amino or hydroxyl, one of the substituents $R^3$ or $R^4$ denotes a hydrogen atom, $(C_1-C_4)$-alkyl, phenyl, pyridyl, furyl, thienyl or benzofuryl and $R^5$ is hydrogen or $(C_1-C_4)$-alkyl, or the radicals $R^3$ or $R^4$ and $R^5$ together form a —$(CH_2)_n$—group, where n=2, 3 or 4, which is optionally substituted by $(C_1-C_4)$-alkyl, (b) the quinoxaline system is bonded to the imidazolidinedione via position 5', 6' or 7' and $R^3$ and $R^4$ denote a hydrogen atom, $(C_1-C_6)$-alkyl, $(C_5-C_7)$-cycloalkyl, phenyl-$(C_1-C_2)$-alkyl, phenyl, pyridyl, furyl, thienyl or benzofuryl, $R^1$ is a hydrogen atom, $R^2$ is a hydrogen atom, $(C_1-C_4)$-alkyl or phenyl and $R^5$ is hydrogen or $(C_1-C_4)$-alkyl, or the radicals $R^3$ and $R^4$ together form a —$(CH_2)_m$—group, where m=3, 4 or 5, which is optionally substituted by $(C_1-C_4)$-alkyl,
and physiologically tolerated salts thereof.

Particularly preferred compounds of the formula I are those in which the quinoxaline ring system is bonded to the imidazolidinedione partial structure in case (a) via position 2' or 3' or in case (b) via position 6' or 7';

in case (a), the substituents $R^1$ and $R^2$ are in positions 6' and 7' and denote a hydrogen atom, $(C_1-C_4)$-alkyl, $(C_1-C_4)$-alkoxy, fluorine, trifluoromethyl, amino or hydroxyl, $R^3$ or $R^4$ denotes a hydrogen atom, $(C_1-C_4)$-alkyl or phenyl and $R^5$ is hydrogen or methyl, or the radicals $R^3$ and $R^5$ or $R^4$ and $R^5$ together form a—$(CH_2)_3$— group which is optionally substituted by $(C_1-C_4)$-alkyl, so that a fused-on six-membered ring is present;

in case (b) the substituents $R^3$ and $R^4$ denote a hydrogen atom, $(C_1-C_6)$-alkyl, $(C_5-C_7)$-cycloalkyl, benzyl, phenyl, furyl or thienyl, $R^1$ is hydrogen, $R^2$ denotes a hydrogen atom, $(C_1-C_4)$-alkyl or phenyl and $R^5$ is hydrogen or methyl, or the radicals $R^3$ and $R^4$ together form a —$(CH_2)_4$— group, so that a six-membered ring fused onto the quinoxaline system is present,
and physiologically tolerated salts thereof.

Alkyl can be straight-chain or branched. $(C_6-C_{12})$-Aryl is understood as, for example, naphthyl or biphenyl, but in particular phenyl.

The compounds of the formula I can be present both in the optically inactive and in the enantiomerically pure form.

The invention furthermore relates to a process for the preparation of compounds of the formula I, which comprises (a) reacting a carbonyl compound of the formula II

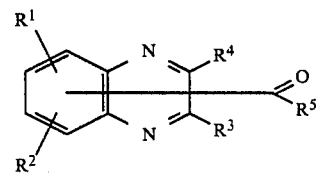

wherein $R^1$, $R^2$, $R^3$, $R^4$ and $R^5$ have the meanings given in the case of formula I, with cyanides, preferably with alkali metal and alkaline earth metal cyanides, and ammonium carbonate to give compounds of the formula I, or (b) reacting a compound of the formula III

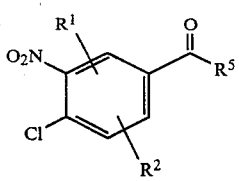

in which R¹ is hydrogen and R² and R⁵ have the meanings given in the case of formula I, with benzylamine

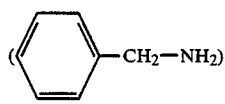

to give a compound of the formula IV

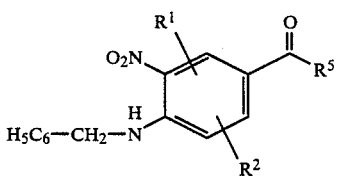

reacting the resulting compound of the formula IV with a cyanide, preferably an alkali metal or alkaline earth metal cyanide, and ammonium carbonate to give a compound of the formula V

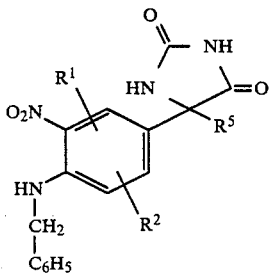

reducing the resulting compound in the presence of a catalyst to give a compound of the formula VI

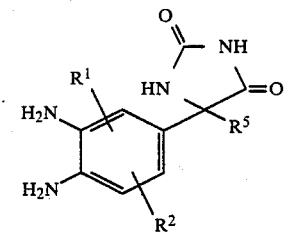

and subsequently reacting this with a dicarbonyl compound VII

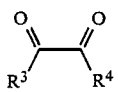

to give a compound of the formula I

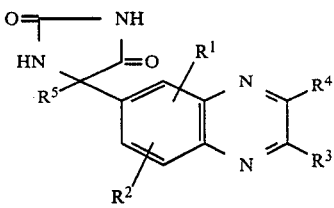

in which $R^1$ denotes hydrogen and $R^2$, $R^3$, $R^4$ and $R^5$ have the meanings given, and, if appropriate, converting the reaction products into physiologically tolerated salts using bases.

The synthesis according to process (a) is advantageously carried out under normal pressure or in an autoclave at temperatures between 50° C. and 160° C. and with reaction times of 1 to 80 hours.

Although the relative amount of the reagents can vary within certain limits, at least a slight excess of the cyanide and ammonium carbonate based on the carbonyl component is preferably used, in order to achieve a good yield.

The carbonyl compound of the formula II is advantageously reacted in each case with an excess of cyanide (1.5 to 3 equivalents) and a larger excess of ammonium carbonate (2 to 5 equivalents) in suitable solvents, such as ethers (for example dioxane or dimethoxyethane), alcohols (for example ethanol, methanol or methoxyethanol) or mixtures of these solvents with water.

Where they have not been described in the literature, the carbonyl-quinoxalines of the formula II (compare, for example, J. Francis et al., Biochem. J. 63 (1956), 455) can be prepared by condensation of suitably substituted phenylenediamines with 1,2-dicarbonyl compounds, with 1,2,3-tricarbonyl compounds or with synthesis equivalents thereof.

Process (b) represents a variant for the preparation of compounds of the formula I which is more favorable in some cases. It comprises first building up the imidazolidine ring system from known precursors of the formula III (literature: for example F. Mayer et al., Chem. Ber. 56 (1932) 1295) and subsequently subjecting this to a condensation reaction with a suitable dicarbonyl component (formula VII, for example hexane-3,4-dione) to give the quinoxaline.

Bases which are used according to the invention as reaction partners for the preparation of the pharmacologically tolerated salts are those which form non-toxic salts with the acid imidazolidinediones of the formula I. The cations of the salts must thereby be non-toxic over the wide range of doses administered. Examples are sodium, potassium, calcium and magnesium ions.

The salts can be prepared by treating, for example, the imidazolidinediones of the formula I with an aqueous solution of the desired pharmacologically tolerated cation and evaporating the resulting solution to dryness—preferably under reduced pressure.

The compounds of the formula I according to the invention have useful pharmacological properties and can be used in therapy as aldose reductase inhibitors for preventing chronic diabetic complications. These include, for example, cataract and retinopathy, peripheral neuropathy, nephropathy, microangiopathy and delayed cornea reepithelialization (P. F. Kador et al., J. Med. Chem. 28, [1985] 841).

The substances have a very high aldose reductase-inhibiting action.

The activity of the compounds according to the invention as active substances for the treatment of chronic diabetic complications is determined by their property of successfully passing one or more of the following biological and/or pharmacological tests:

1. in vitro inhibition of the enzyme activity of isolated aldose reductase;
2. in vitro inhibition of the sorbitol accumulation in erythrocytes in the lens or in the sciatic nerve of normal or streptozotocin-diabetic rats;
3. reduction of increased sorbitol levels in streptozotocin-diabetic rats in vivo;
4. prevention or inhibition of galactitol formation in lenses of galactosemic rats or dogs;
5. prevention of cataract formation and reduction in cataract in galactosemic and diabetic rats or dogs;
6. normalization of the nerve conduction velocity in diabetic experimental animals;
7. prevention of the basal membrane thickening of diabetic experimental animals.

The test methods are described in principle in the literature.

For some compounds according to the invention, a high activity was to be observed in several tests.

Test No. 1

In vitro inhibition of enzyme activity (rat hepatic enzyme preparation)

The inhibiting values on aldose reductase are summarized in Table 1 for some compounds according to the invention ($IC_{50}$ [M] denotes the molar concentration of the compound which is required for 50% inhibition).

TABLE 1

| Compound according to Example No. | $IC_{50}$ [M] |
| --- | --- |
| 2 | $1.2 \times 10^{-6}$ |
| 18 | $2.8 \times 10^{-4}$ |
| 19 | $7.3 \times 10^{-6}$ |
| 20 | $3.6 \times 10^{-7}$ |
| 21 | $1.5 \times 10^{-4}$ |
| 22 | $4.4 \times 10^{-4}$ |
| 23 | $1.4 \times 10^{-5}$ |
| 26 | $2.8 \times 10^{-4}$ |
| 33 | $2.7 \times 10^{-9}$ |

Test No. 2

In vitro inhibition of sorbitol accumulation (tissue of normal rats)

The inhibiting values summarized in Table 2 were determined for some of the compounds according to the invention at a concentration of 3 μmol/l.

TABLE 2

| Compound according to Example No. | Nerve [%] | Erythrocytes [%] |
| --- | --- | --- |
| 2 | −30 | |
| 18 | −39 | −10 |
| 20 | | −29 |
| 21 | −38 | −26 |
| 23 | −65 | −21 |
| 33 | −30 | −26 |

Test No. 3

Reduction of increased sorbitol levels

The oral administration in ®Tylose suspension (=suspension of a water-soluble cellulose ether), of the substances mentioned as examples in the following Table 3 to streptozotocin-diabetic rats leads to a great reduction in the sorbitol accumulation in erythrocytes and in the nerve tissue in comparison with untreated control animals.

TABLE 3

| Compound according to Example No. | Dose | Sorbitol content after 5 hours in | |
| --- | --- | --- | --- |
| | | erythrocytes | nerve tissue |
| 2 | 25 mg/kg | −57% | −22% |
| 23 | 25 mg/kg | −72% | −83% |
| 25 | 25 mg/kg | −66% | −70% |

On the basis of their pharmacological activities, the compounds of the formula I according to the invention or their salts are used as medicaments, in particular for inhibition of aldose reductase. The invention thus also relates to the use of the compounds of the formula I as medicaments.

The new compounds and salts thereof can be used as medicaments either by themselves or together with physiologically tolerated auxiliaries or excipients. For this purpose, they can be administered enterally in doses of [0.05 to 5.0] mg/(kg day), preferably [0.5 to 2.5] mg/(kg day) or parenterally in doses of [0.005 to 0.5] mg/(kg day), preferably [0.05 to 0.25]mg/(kg day).

The dosage can also be increased in severe cases, but in many cases smaller doses are already sufficient.

The substances of the formula I can additionally be used locally for the abovementioned purposes, where they relate to the eye, via a suitable ophthalmic solution which can be used on the eye in the form of drops.

The invention thus also relates to pharmaceutical preparations which contain a compound of the formula I or a salt thereof in a physiologically acceptable excipient, and processes for the production of these preparations, which comprise bringing the substances mentioned into a suitable presentation form together with the excipient and also auxiliaries or additives.

For the oral use form, the compounds of the formula I are mixed with the substances suitable for this and the mixture is brought by customary methods into suitable presentation forms, such as, for example, tablets, push-fit capsules, aqueous alcoholic or oily suspensions or aqueous alcoholic or oily solutions. Inert excipients which can be used are, for example, magnesium carbonate, lactose or maize starch. For tablets, the compounds can be formulated as dry or moist granules. Possible oily excipients or solvents are vegetable or mineral oils, such as, for example, sunflower oil, olive oil or paraffin oil.

For parenteral administration, the active compounds or physiologically tolerated salts thereof are suspended or dissolved with organic or inorganic bases, such as, for example, triethanolamine, cyclohexylamine or sodium or potassium hydroxide, in the substances customary for this. Possible solvents for intravenous use are, for example, water or physiological saline solution, to which further additives, such as alcohol (for example propanediol or glycerol) and sugar solutions (for example glucose or mannitol) can be added.

The following examples serve to illustrate the present invention without limiting it to the substances mentioned here as representatives.

EXAMPLE 1

5-(2',3'-Dimethyl-quinoxalin-6'-yl)-5-methyl-imidazolidine-2,4-dione

A mixture of 3.67 g (18.3 mmol) of 2,3-dimethyl-6-acetylquinoxaline, 1.79 g (27.5 mmol) of potassium cyanide and 7.05 g (73.3 mmol) of ammonium carbonate in 20 ml of ethanol/water =3:1 is heated at 90° C. in an autoclave for 10 hours. After cooling, the mixture is concentrated, diluted with water and neutralized with half-concentrated hydrochloric acid, while stirring and cooling with ice. The solid which has precipitated is separated off and dissolved in methanol/water and the solution is treated with active charcoal, filtered off with suction and concentrated. The product crystallizes out after addition of diethyl ether.

Melting point: 198°–200° C.

EXAMPLE 2

5-(2',3'-Diethyl-quinoxalin-6'-yl)-5-methyl-imidazolidine2,4-dione

A mixture of 11.9 g (0.05 mol) of 2,3-diethyl-6-acetyl-quinoxaline, 4.90 g (0.075 mol) of potassium cyanide and 19.2 g (0.20 mol) of ammonium carbonate are heated in 100 ml of ethanol/water =3:1 at 90° C. in an autoclave for 10 hours. After cooling, the precipitate formed is dissolved with a little water and the alcohol is largely distilled off in vacuo. The precipitate is filtered off with suction, washed with water and dried in vacuo over phosphorus pentoxide.

Melting point: 212°–213° C.

EXAMPLE 3

5-(2',-3'-Di-n-pentyl-quinoxalin-6'-yl)-5-methyl-imidazolidine-2,4-dione

In accordance with Example 2, from 6-acetyl-2,3-di-n-pentylquinoxaline.

Melting point: 153°–155° C.

EXAMPLE 4

5-(2',3'-Diisopropyl-quinoxalin-6'-yl)-5-methyl-imidazolidine-2,4-dione

In accordance with Example 2, from 6-acetyl-2,3-diisopropylquinoxaline.

Melting point: 210°–212° C.

EXAMPLE 5

5-(2',3'-Diethyl-7'-methyl-quinoxalin-6'-yl)-5-methyl-imidazolidine-2,4-dione Analogously to Example 2, from 6-acetyl-2,3-diethyl-7methylquinoxaline.

Melting point: 228°–229° C.

EXAMPLE 6

5-Methyl-5-(1',2',3',4'-tetrahydrophenazin-7'-yl)-imidazolidine-2,4-dione

Analogously to Example 2, from 7-acetyl-1,2,3,4-tetrahydrophenazine.

Melting point: 196°–202° C.

EXAMPLE 7

5-[2',3'-(Difuran-2''-yl)-quinoxalin-6'-yl]-5-methyl-imidazolidine-2,4-dione In accordance with Example 2, from 6-acetyl-2,3-(difuran-2'-yl)-quinoxaline.

Melting point: 265° C. (decomposition).

EXAMPLE 8

5-(2',3'-Diphenyl-quinoxalin-6'-yl)-5-methyl-imidazolidine-2,4-dione

From 6-acetyl-2,3-diphenyl-quinoxaline, analogously to Example 2.

Melting point: 316° C. (decomposition).

EXAMPLE 9

5-Methyl-5-(2'-phenyl-quinoxalin-6'-yl)-imidazolidine-2,4-dione

Analogously to Example 2, from 6-acetyl-2-phenyl-quinoxaline. Melting point: 269°–271° C.

EXAMPLE 10

5-(2',3'-Diethyl-quinoxalin-5'-yl)-5-methyl-imidazolidine-2,4-dione

Analogously to Example 2, from 5-acetyl-2,3-diethyl-quinoxaline.

Melting point: 216°–217° C.

EXAMPLE 11

5-Methyl-5-(2',3'-pentamethylene-quinoxalin-5'-yl)-imidazolidine-2,4-dione

From 5-acetyl-2,3-pentamethylene-quinoxaline, in accordance with Example 2.

Melting point: 296°–298° C.

EXAMPLE 12

5-(2',3'-Diethyl-7'-methyl-quinoxalin-6'-yl)-5-propyl-imidazolidine-2,4-dione In accordance with Example 2, from 6-butyryl-2,3-diethyl-7-methyl-quinoxaline.

Melting point: 217°–219° C.

EXAMPLE 13

(a) 5-Methyl-5-(2'-thienyl-quinoxalin-6'-yl)-imidazolidine-2,4-dione and
(b) 5-Methyl-5-(3'-thienyl-quinoxalin-6'-yl)-imidazolidine-2,4-dione In accordance with Example 2, from 6-acetyl-2/3-thienylquinoxaline, two products with melting points of 273°–274° C. and 256°–258° C. are obtained after crystallization; unambiguous allocation of the isomers is currently not possible with the spectroscopic methods available.

EXAMPLE 14

5-Methyl-5-(1'4'-methylene-1',2',3',4'-tetrahydrophenazin-7'-yl)-imidazolidine-2,4-dione In accordance with Example 2, from 7-acetyl-1,4-methylene-1,2,3,4-tetrahydro-phenazine.

Melting point: 307°–308° C.

EXAMPLE 15

5-(2'3'-Diethyl-quinoxalin-6'-yl)-5-phenyl-imidazolidine-2,4-dione

A mixture of 14.5 g (0.05 mol) of 6-benzoyl-2,3-diethylquinoxaline, 4.9 g (0.075 mol) of potassium cyanide and 20 g (0.208 mol) of ammonium carbonate in 100 ml of ethanol/water (7:3) is heated at 110° C. in an autoclave for 15 hours. After cooling, the insoluble constituents are filtered off and the filtrate is evaporated in vacuo.

The residue is taken up in about 300 ml of 1N sodium hydroxide solution, the mixture is treated with active charcoal and the aqueous solution is filtered and extracted three times by shaking with 120 ml of ether each time. The aqueous phase is treated with active charcoal again and filtered. The filtrate is neutralized with half-concentrated hydrochloric acid and the solid which has precipitated is filtered off with suction and washed thoroughly with water. The substance is recrystallized from ethanol/water.

Melting point: 231°–232° C.

EXAMPLE 16

5-(2',3'-Dimethyl-quinoxalin-6'-yl)-5-phenyl-imidazolidine-2,4-dione

In accordance with Example 15, from 6-benzoyl-2,3-dimethylquinoxaline.

Melting point: 267°–269° C.

Example 17

5-(Quinoxalin-6'-yl)-5-methyl-imidazolidine-2,4-dione (a) 4-Benzylamino-3-nitro-acetophenone 29.9 g (0.15 mol) of 4-chloro-3-nitro-acetophenone are dissolved in 90 ml of benzylamine and heated at 90° C. for about 20 minutes. When the reaction is complete (thin-layer chromatogram) the yellow-brown solution is acidified using half-concentrated hydrochloric acid while stirring and cooling with ice, and the precipitated product is taken up in ethyl acetate. The aqueous phase is extracted repeatedly with ethyl acetate, and the combined organic phases are washed with water and saturated sodium chloride solution, dried over sodium sulfate and evaporated in vacuo. The residue is recrystallized from methanol/water/dioxane.

Melting point 103°–107° C.

(b) 5-(4'-Benzylamino-3'-nitro-phenyl)-5-methyl-imidazolidine-2'4-dione 40.5 g (0.15 mol) of 4-benzylamino-3-nitro-acetophenone are heated at 100° C. in an autoclave for 18 hours in a mixture comprising 170 ml of ethanol, 60 ml of water, 14.6 g of potassium cyanide and 58 g of ammonium carbonate. The alcohol is largely evaporated off in vacuo, the mixture remaining is diluted with water, and the product is filtered off under suction and washed with water. The product is recrystallized from ethanol/water with addition of active charcoal.

Melting point: 190°–192° C.

(c) A solution of 11.4 g (33.5 mmol)of 5-(4'-benzylamino-3'-nitro-phenyl)-5-methyl-imidazolidine-2,4-dione in 350 ml of methanol is hydrogenated at room temperature in the presence of 7.0 g of palladium/charcoal (5%) until the uptake of hydrogen has ended. The catalyst is filtered off and washed thoroughly with methanol and the filtrate is evaporated in vacuo.

2.2 g of the substance thus obtained are dissolved in 24 ml of methanol/dioxane (5:1), 1.5 ml of a 40% strength aqueous glyoxal solution are added and the mixture is heated at 45 to 50° C. for 1 hour. When the reaction has ended (thin layer chromatogram), the solvent is evaporated off in vacuo, the residue is dissolved in 1N sodium hydroxide solution and the solution is treated with active charcoal, acidified with 2N hydrochloric acid and extracted three times with ethyl acetate. The combined organic phases are washed with water and saturated sodium chloride solution, dried over sodium sulfate and concentrated in vacuo. The residue is recrystallized from acetone/diisopropyl ether.

Melting point: 126°–129° C.

EXAMPLE 18

5-(Quinoxalin-2'-yl)-5-methyl-imidazolidine-2,4-dione 4.9 g (28.5 mmol) of 2-acetyl-quinoxaline, 3.88 g (60 mmol) of potassium cyanide and 13.62 g (0.14 mol) of ammonium carbonate are suspended in 60 ml of ethanol/water 4:1 and the suspension is stirred at 140° C. in an autoclave for 5 hours. After cooling, water is added until the residue dissolves and the solution is carefully acidified (pH=5–6) with half-concentrated hydrochloric acid while cooling with ice. The precipitate formed is filtered off with suction, washed with water and recrystallized from methanol.

Melting point: 229° C.

EXAMPLE 19

5-(6',7'-Dimethyl-quinoxalin-2'-yl)-5-methyl-imidazolidine-2,4-dione

In accordance with Example 18, from 2-acetyl-6,7-dimethylquinoxaline, 8 hours at 135° C. in an autoclave.

Melting point: 220° C.

EXAMPLE 20

5-Methyl-5-(3',6',7'-trimethyl-quinoxalin-2'-yl)-imidazolidine-2,4-dione hydrate In accordance with Example 18, from 2-acetyl-3,6,7-trimethyl-quinoxaline, 8 hours at 140° C. in an autoclave.

Melting point: 145°–147° C. (decomposition).

EXAMPLE 21

5-(6',7'-Dimethoxy-quinoxalin-2'-yl)-5-methyl-imidazolidine-2,4-dione

Analogously to Example 18, from 2-acetyl-4,7-dimethyl-quinoxaline, 8 hours at 140° C., recrystallization from ethanol/methylglycol.

Melting point: 290° C..

Example 22

5-Methyl-5-(3'-phenyl-quinoxalin-2'-yl)-imidazolidine-2,4-dione

In accordance with Example 18, from 2-acetyl-3-phenylquinoxaline, 12 hours at 140° C. in an autoclave.

Melting point: 238° C. (decomposition).

EXAMPLE 23

5-Methyl-5-(3'-methyl-quinoxalin-2'-yl)-imidazolidine-2,4-dione 25 g (0.134 mol) of 2-acetyl-3-methyl-quinoxaline, 17.5 g (0.268 mol) of potassium cyanide and 64.4 g (0.67 mol) of ammonium carbonate are dissolved in 445 ml of ethanol/ water 1:1 and the solution is stirred at 60° C. for 72 hours. When the reaction has ended, the mixture is carefully acidified with half-concentrated hydrochloric acid, while cooling with ice, and is subsequently stirred and the precipitate formed is filtered off with suction. The residue is washed with water and taken up in 1N sodium hydroxide solution and the mixture is extracted by shaking with ether. The product is liberated by acidification with half-concentrated hydrochloric acid, while cooling with ice. It is filtered off with suction, washed with water and recrystallized from ethanol or methanol/ethyl acetate 1:1.

Melting point: 225°–227° C.

Example 24

5-Methyl-5-(3'-methyl-6'/7'-trifluoromethyl-quinoxalin-2'-yl)-imidazolidine-2,4-dione Analogously to Example 23, from 2-acetyl-6/7-trifluoromethyl-quinoxaline. Recrystallization from ethyl acetate/hexane.

Melting point: 217° C., a uniform product according to the high pressure liquid chromatogram; the precise allocation of the substitution into the 6- or 7-position is currently not possible with the methods available.

EXAMPLE 25

5-(6'/7'-Fluoro-quinoxalin-2'-yl)-5-methyl-imidazolidine-2,4-dione

In accordance with Example 18, from 2-acetyl-6/7-fluoroquinoxaline.
Melting point: 221° C.

EXAMPLE 16

5-(6'/7'-Fluoro-3'-methyl-quinoxalin-2'-yl)-5-methyl-imidazolidine-2,4-dione

Analogously to Example 24, from 2-acetyl-6/7-fluoroquinoxaline.
Melting point: 271° C.

EXAMPLE 27

5-(6'/7'-Amino-3'-ethyl-quinoxalin-2'-yl)-5-methyl-imidazolidine-2,4-dione

In accordance with Example 24, from 2-acetyl-6/7-aminoquinoxaline.
Melting point: 260°–263° C.

Example 28

5-(6'/7'-Hydroxy-3'-methyl-quinoxalin-2'-yl)-5-methyl-imidazolidine-2,4-dione

In accordance with Example 24, from 2-acetyl-6/7-phenyl-sulfonyloxy-quinoxaline;
Melting point: 268°–271° C.

EXAMPLE 29

Spiro [imidazolidine-5,1'-(1',2',3',4'-tetrahydro-phenazine)]-2,4-dione

In accordance with Example 23, from 1,2,3,4-tetrahydro-phenazin-1-one.
Melting point: 295° C. (decomposition).

EXAMPLE 30

Spiro [imidazolidine-5,1'-(3',3'-dimethyl-1',2',3',4'-tetrahydrophenazine)]-2,4-dione In accordance with Example 18, from 3,3-dimethyl-1,2,3,4-tetrahydro-phenazin-1-one.
Melting point: 281° C.

EXAMPLE 31

Spiro [imidazolidine-5,1'-(8'fluoro-3',3'-dimethyl-1',2',3',4'-tetrahydro-phenazine)]-2,4-dione From 8-fluoro-3,3-dimethyl-1,2,3,4-tetrahydro-phenazin-1-one, analogously to Example 18.
Melting point: 292° C.

EXAMPLE 32

(−)-5-Methyl-5-(3'-methyl-quinoxalin-2'-yl)-imidazolidine-2,4-dione 10 g (39 mmol) of (+/−)-5-methyl-5-(3'-methyl-quinoxalin-2'-yl)-imidazolidine-2,4-dione and 16.8 g (39 mmol) of brucine dihydrate are dissolved in 75 ml of absolute ethanol at the boiling point. The solution is left to cool slowly. The brucine salt which has crystallized out is filtered off with suction, dried in vacuo and re-crystallized again several times from about the same volume of solvent, with slow cooling, until the amount of dry residue approximately corresponds to 1/5 to ¼ of the amount of substance employed. The salt thus obtained can be split by column filtration over silica gel using ethyl acetate/methanol (1:1). Brucine is recovered by using methanol/triethylamine.

The title compound is obtained by fractional crystallization from ethyl acetate/methanol (1:1); melting point: 203°–204° C., $[\alpha]_D = -52.4°$ C.

EXAMPLE 33

(+)-5-Methyl-5-(3'-methyl-quinoxalin-2'-yl)-imidazolidine-2,4-dione

The mother liquor of the first crystallization from Example 32 is freed from the solvent in vacuo. The residue is heated in about 50 ml of absolute ethanol, seed crystals of the salt of brucine and levo-rotatory enantiomer are added to the solution and the mixture is cooled slowly.

The salt which has crystallized out is filtered off with suction and the mother liquor is evaporated. This procedure is repeated until the amount of dry residue after the evaporation approximately corresponds to 1/5 to ¼ of the amount of substance originally employed in Reaction Example 32. The resulting salt is then split analogously to Example 32. The title compound is obtained by fractional crystallization of the crude product from ethyl acetate/methanol (1:1).
Melting point: 203°–204° C., $[\alpha]_D = +52.5°$ C.

We claim:
1. A 5-quinoxalyl-imidazolidine-2,4-dione of the formula I

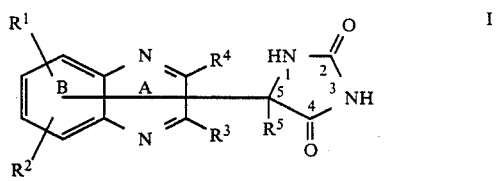

in which
the quinoxaline ring system is bonded to the imidazolidinedione via position 2',3',5',6',7' or 8',
$R^1$ $R^2$ are identical or different and are hydrogen, $(C_1-C_6)$-alkyl, $(C_5-C_7)$-cycloalkyl, phenyl-$(C_1-C_4)$-alkyl, naphthyl-$(C_1-C_4)$-alkyl, naphthyl, biphenyl, phenyl, pyridyl, furyl, thienyl, benzofuryl, $(C_1-C_4)$-alkoxy, halogen, halogeno-$(C_1C_4)$-alkyl, nitro, amino or hydroxyl;
$R^3$ and $R^4$ are identical or different and are hydrogen $(C_1-C_6)$-alkyl, $(C_5-C_7)$-cycloalkyl, phenyl-$(C_1-C_4)$-alkyl, naphthyl-$(C_1-C_4)$-alkyl, naphthyl, biphenyl, phenyl, pyridyl, furyl, thienyl, benzofuryl, $(C_1-C_4)$-alkoxy, halogen, halogeno-$(C_1C_4)$-alkyl, nitro, amino or hydroxyl;

$R^5$ is a hydrogen atom, $(C_1-C_6)$-alkyl, $(C_5-C_7)$-cycloalkyl, phenyl-$(C_1-C_4)$-alkyl, naphthyl-$(C_1-C_4)$-alkyl, naphthyl, biphenyl or phenyl, with the exception of the compound wherein at the same time $R^1$, and $R^2$ and $R^5$ are each hydrogen, $R^3$ and $R^4$ are each methyl, and the quinoxaline ring system is bonded to the imidazolidinedione via position 6;

or a physiologically tolerated salt thereof.

2. A compound of the formula I as claimed in claim 1, in which (a) the quinoxaline ring system is bonded to the imidazolidinedione via position 2' or 3' and $R^1$ and $R^2$ are in positions 6' and 7' respectively and are hydrogen, $(C_1-C_4)$-alkyl, phenyl, $(C_1-C_4)$-alkoxy, halogen, halogeno-$(C_1-C_4)$-alkyl, amino or hydroxyl, one of the substituents $R^3$ or $R^4$ is a hydrogen atom, $(C_1-C_4)$-alkyl, phenyl, pyridyl, furyl, thienyl or benzofuryl and $R^4$ is hydrogen or $(C_1-C_4)$-alkyl, or (b) the quinoxaline system is bonded to the imidazolidinedione via position 5', 6' or 7' and $R^3$ and $R^4$ are a hydrogen atom, $(C_1-C_6)$-alkyl, $(C_5-C_7)$-cycloalkyl, phenyl-$(C_1-C_2)$-alkyl, phenyl, pyridyl, furyl, thienyl or benzofuryl, $R^1$ is a hydrogen atom, $R^2$ is a hydrogen atom, $(C_1-C_4)$-alkyl or phenyl and $R^5$ is hydrogen or $(C_1-C_4)$-alkyl, or a physiologically tolerated salt thereof.

3. A compound of the formula I as claimed in claim 1, in which (a) the quinoxaline ring system is bonded to the imidazolidinedione ring structure via position 2' or 3' and the substituents $R^1$ and $R^2$ are in positions 6' and 7' and are a hydrogen atom, $(C_1-C_4)$-alkyl, $(C_1-C_4)$-alkoxy, fluorine, trifluoromethyl, amino or hydroxyl, $R^3$ $R^4$ is a hydrogen atom, $(C_1-C_4)$-alkyl or phenyl and $R^5$ is hydrogen or methyl, or (b) the quinoxaline ring system is bonded to the imidazolidinedione ring structure via position 6' or 7' and the substituents $R^3$ and $R^4$ are a hydrogen atom, $(C_1-C_6)$-alkyl, $(C_5-C_7)$-cycloalkyl, benzyl, phenyl, furyl or thienyl, $R^1$ is hydrogen, $R^2$ is a hydrogen atom, $(C_1-C_4)$-alkyl or phenyl and $R^5$ is hydrogen or methyl, or a physiologically tolerated salt thereof.

4. A pharmaceutical composition for the inhibition of the aldose reductase which comprises a compound of the formula I as claimed in claim 1 or a physiologically tolerated salt thereof together with a physiologically tolerated carrier.

5. A method for the treatment of a patient needing an inhibition of the aldose reductase which comprises administering an effective amount of a compound of the formula I as claimed in claim 1.

* * * * *